United States Patent [19]

Kishkovich et al.

[11] Patent Number: 6,096,267
[45] Date of Patent: Aug. 1, 2000

[54] SYSTEM FOR DETECTING BASE CONTAMINANTS IN AIR

[75] Inventors: Oleg P. Kishkovich, Smithfield; Devon A. Kinkead, Cumberland, both of R.I.

[73] Assignee: Extraction Systems, Inc., Franklin, Mass.

[21] Appl. No.: 08/795,949

[22] Filed: Feb. 28, 1997

[51] Int. Cl.[7] .................................................. G01N 21/76
[52] U.S. Cl. .............................. 422/52; 422/62; 422/93; 436/111
[58] Field of Search .................................. 422/91, 93, 62, 422/52; 436/116, 111, 113, 172

[56] References Cited

U.S. PATENT DOCUMENTS

| | | | |
|---|---|---|---|
| 3,647,387 | 3/1972 | Benson et al. | 23/232 R |
| 3,727,029 | 4/1973 | Chrow | 219/301 |
| 3,787,184 | 1/1974 | Novak et al. | 23/230 R |
| 3,807,233 | 4/1974 | Crawford | 73/421 |
| 3,904,371 | 9/1975 | Neti et al. | 23/232 R |
| 3,911,413 | 10/1975 | Wallace | 340/237 R |
| 3,919,397 | 11/1975 | Gould | 423/405 |
| 3,967,933 | 7/1976 | Etess et al. | 23/232 |
| 3,996,008 | 12/1976 | Fine et al. | 23/254 R |
| 4,049,383 | 9/1977 | Burton et al. | 23/232 |
| 4,059,409 | 11/1977 | Barto et al. | 23/284 |
| 4,070,155 | 1/1978 | Fraim | 23/230 PC |
| 4,154,586 | 5/1979 | Jones et al. | 55/274 BN |
| 4,301,114 | 11/1981 | Rounbehler et al. | 422/52 |
| 4,333,735 | 6/1982 | Hardy et al. | 23/232 R |
| 4,333,752 | 6/1982 | Thies et al. | 55/387 |
| 4,381,408 | 4/1983 | Rounbehler et al. | 564/112 |

(List continued on next page.)

FOREIGN PATENT DOCUMENTS

| | | |
|---|---|---|
| 1201646 | 3/1986 | Canada . |
| 214213 | 10/1984 | Germany . |
| 58-085155 | 5/1983 | Japan . |
| 63-24149 | 5/1986 | Japan . |
| 4-50756 | 2/1992 | Japan . |
| 5-45289 | 2/1993 | Japan . |
| 4-315048 | 3/1993 | Japan . |
| 5-302895 | 11/1993 | Japan . |
| 6-118077 | 4/1994 | Japan . |

OTHER PUBLICATIONS

Thermo Environmental Instruments Inc., Model 17 Chemiluminescence $NH_3$ Analyzer Instruction Manual, 1994.

Viewgraph, "Compact Chemiluminescent $NO/NO_x$ Stack Gas Analyzer," Instrumatic International, received by one of the inventors on Nov. 21, 1997.

Primary Examiner—Jeffrey Snay
Attorney, Agent, or Firm—Fish & Richardson PC

[57] ABSTRACT

A system for detection of base contamination at low concentrations in air comprises a detector that provides a single reading that is stoichiometrically related to the aggregate proton-bonding characteristic of various base contaminants present in the air. The system can operate as a "total amine detector" for air-borne amines, and in important implementations is employed in semiconductor manufacturing, e.g. in respect of incoming or exhaust air from a cleanroom or in respect of the stepper or coat and develop track of a photolithographic process. The system comprises a converter for converting all amines present in the air to a common detectable compound detected by the detector. In various implementations additional features are shown. The converter is located near a sample region of a process and the detector is remotely located with sample lines extending between converter and detector to conduct a sample flow. Filters provide air free of amine contaminants to various stages of a process. The air from the outlet of the filters is employed to provide zero air for calibration of the converter and detector. Continual, automated recalibration is shown. Air from the intermediate port of the filters and air from the outlet are employed to monitor the remaining filter capacity and to verify the fidelity of the zero air reference. In other implementations, the detection system is constructed as a mobile detection unit. In another implementation, the detection system is constructed to monitor total amine concentration at selected stages of a multistage manufacturing process.

24 Claims, 10 Drawing Sheets

U.S. PATENT DOCUMENTS

| | | | |
|---|---|---|---|
| 4,432,939 | 2/1984 | Watanabe et al. | 436/113 |
| 4,473,282 | 9/1984 | Michlin | 354/300 |
| 4,530,272 | 7/1985 | Stokes | 96/34.5 |
| 4,701,306 | 10/1987 | Lawrence et al. | 422/101 |
| 4,714,482 | 12/1987 | Polak et al. | 55/158 |
| 4,726,824 | 2/1988 | Staten | 55/274 |
| 4,737,173 | 4/1988 | Kudirka et al. | 55/276 |
| 4,775,633 | 10/1988 | Rounbehler et al. | 436/106 |
| 4,847,594 | 7/1989 | Stetter | 340/540 |
| 4,873,970 | 10/1989 | Freidank et al. | 128/202.22 |
| 4,890,136 | 12/1989 | Greene et al. | 355/27 |
| 4,921,651 | 5/1990 | Polak et al. | 264/41 |
| 4,946,480 | 8/1990 | Hanville | 55/270 |
| 5,009,678 | 4/1991 | Bikson et al. | 55/16 |
| 5,014,009 | 5/1991 | Arimoto et al. | 324/468 |
| 5,053,064 | 10/1991 | Hama et al. | 55/270 |
| 5,057,436 | 10/1991 | Ball | 436/113 |
| 5,061,296 | 10/1991 | Sengpiel et al. | 55/4 |
| 5,185,268 | 2/1993 | Bonometti et al. | 436/114 |
| 5,208,162 | 5/1993 | Osborne et al. | 436/6 |
| 5,246,668 | 9/1993 | MacCallum et al. | 436/116 |
| 5,288,306 | 2/1994 | Aibe et al. | 95/141 |
| 5,322,797 | 6/1994 | Mallow et al. | 436/106 |
| 5,325,705 | 7/1994 | Tom | 73/31.03 |
| 5,356,594 | 10/1994 | Neel et al. | 422/54 |
| 5,418,170 | 5/1995 | Rounbehler et al. | 436/111 |
| 5,427,610 | 6/1995 | Croker | 95/114 |
| 5,434,644 | 7/1995 | Kitano et al. | 355/30 |
| 5,567,623 | 10/1996 | Rounbehler et al. | 436/158 |
| 5,582,865 | 12/1996 | Rezuke et al. | 427/244 |
| 5,856,198 | 1/1999 | Joffe et al. | 436/100 |

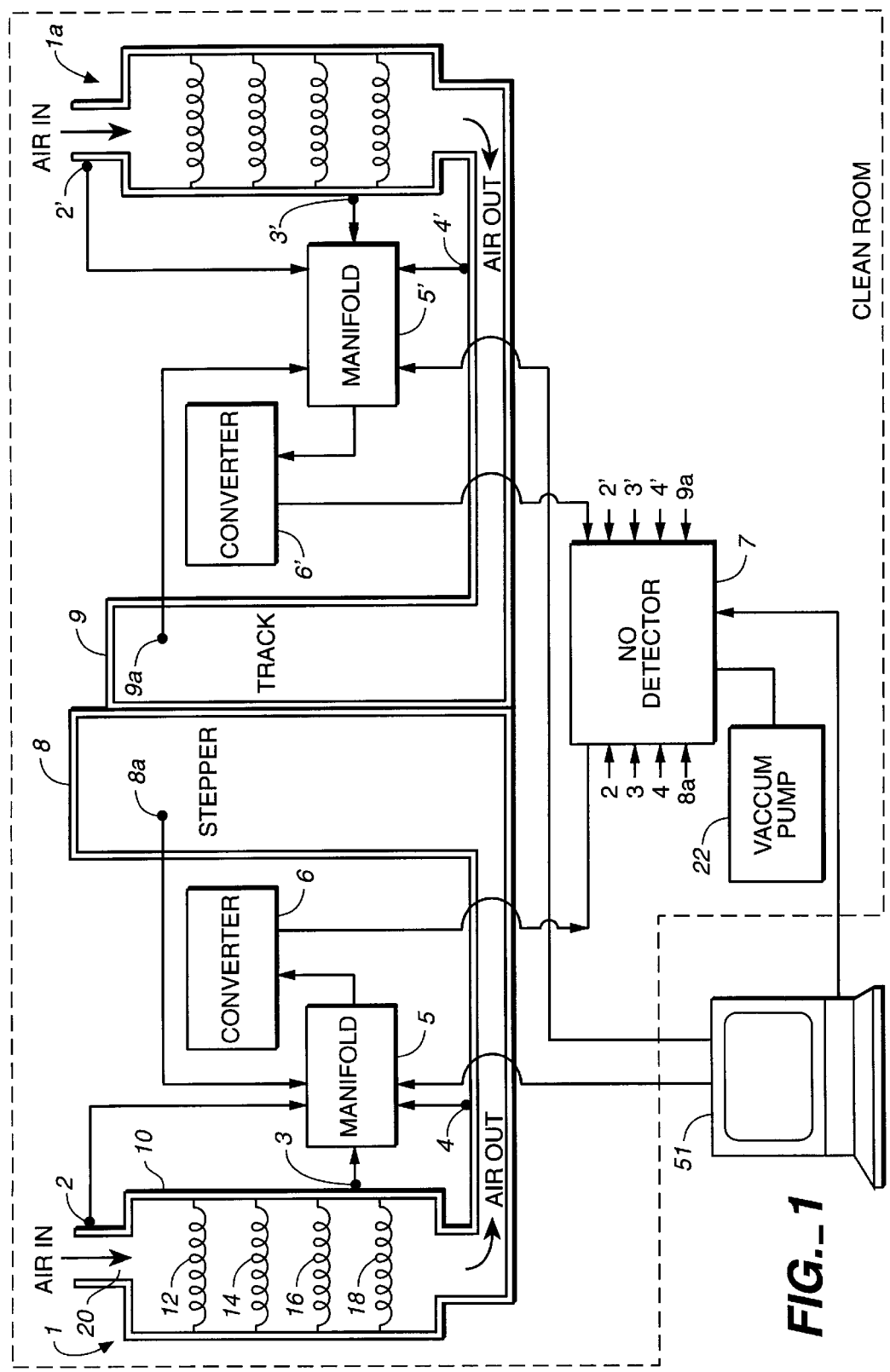
FIG._1

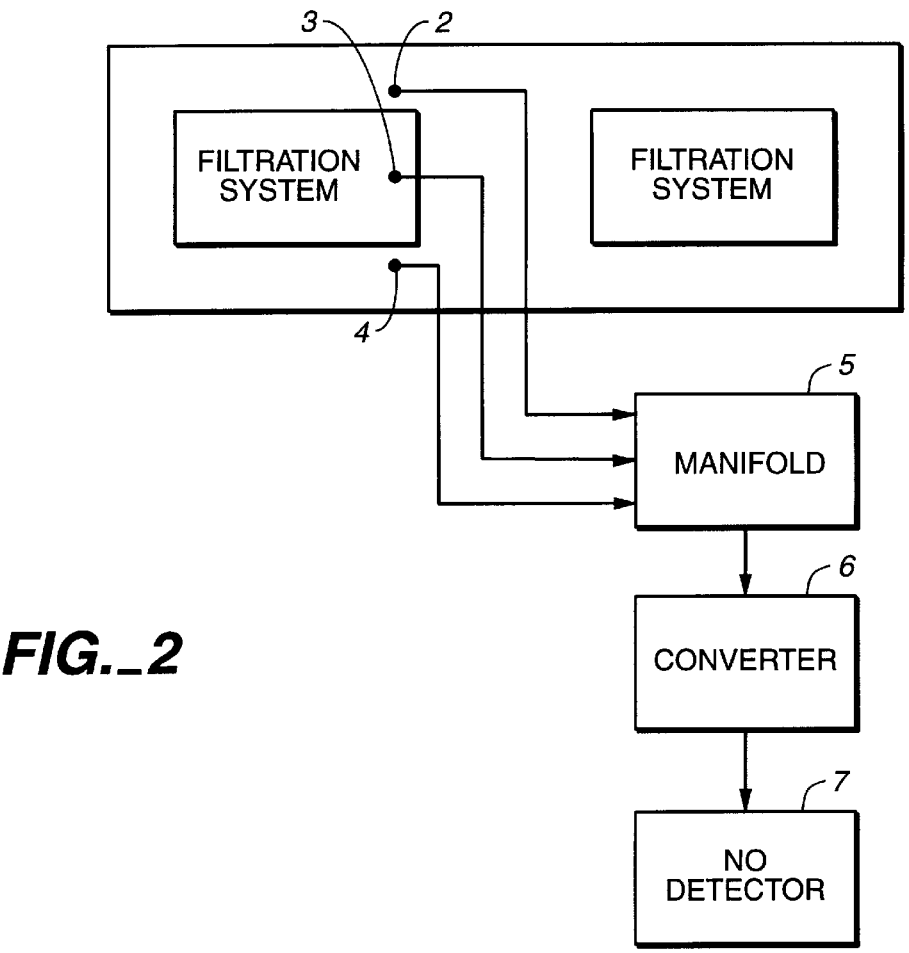
FIG._2
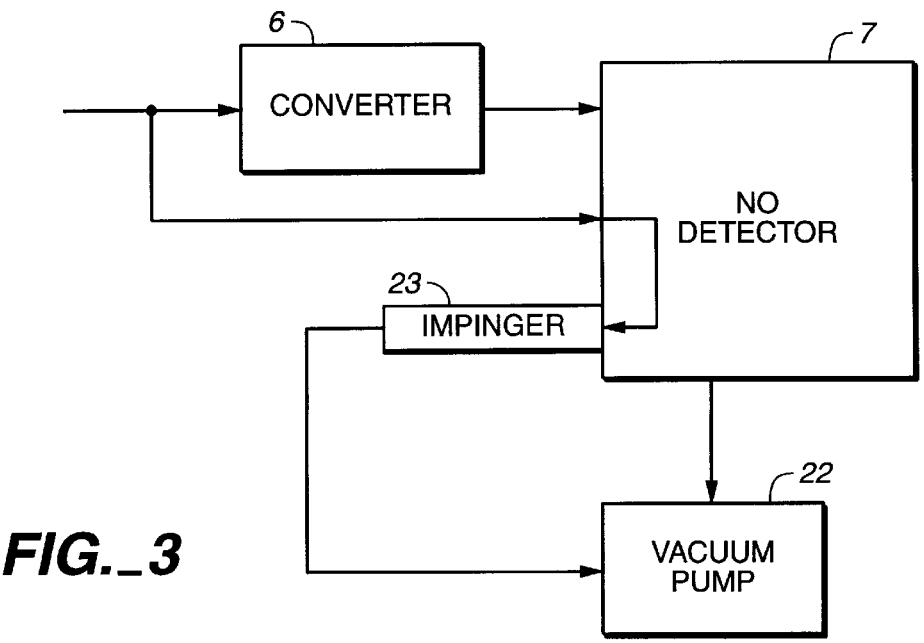
FIG._3

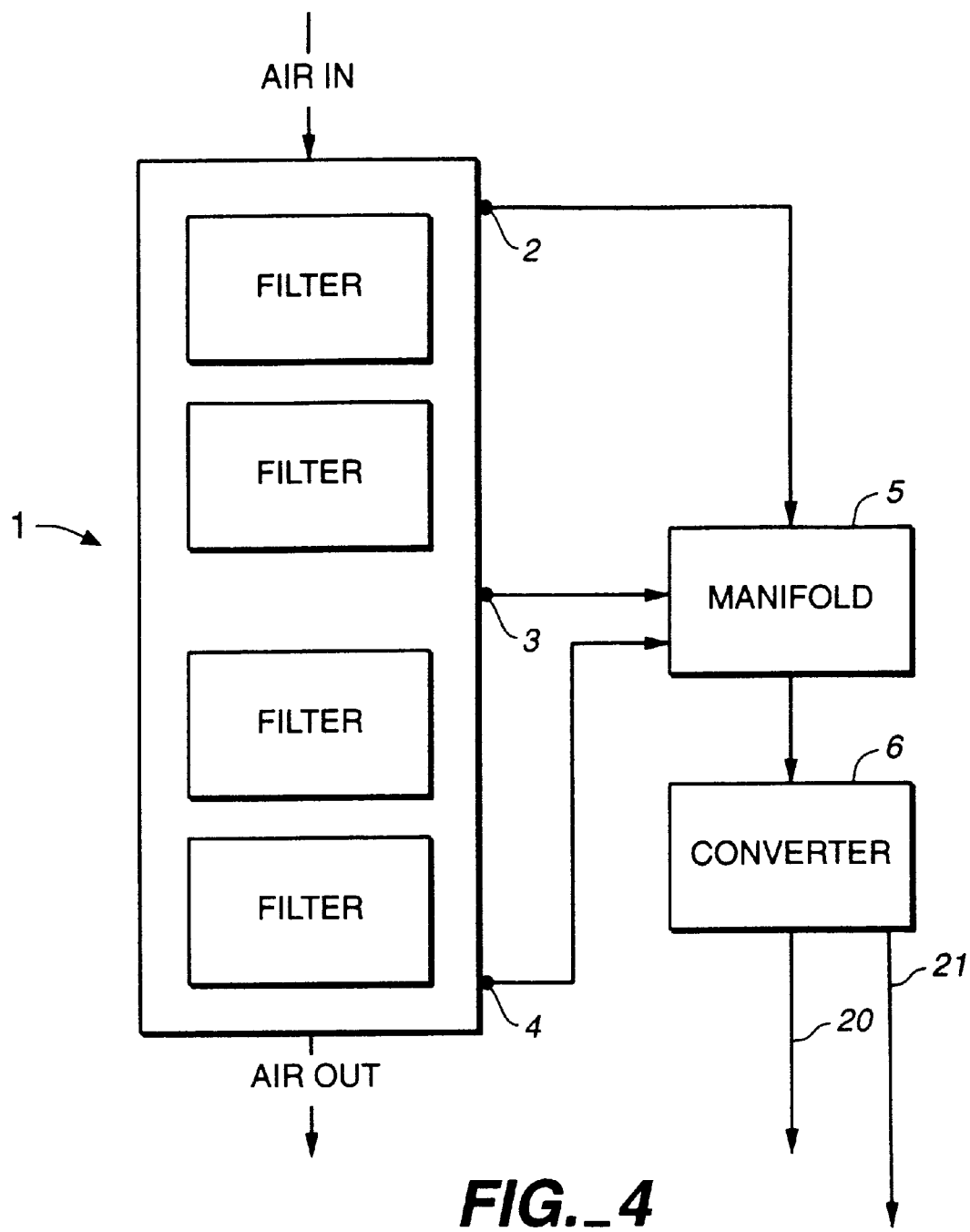
FIG._4

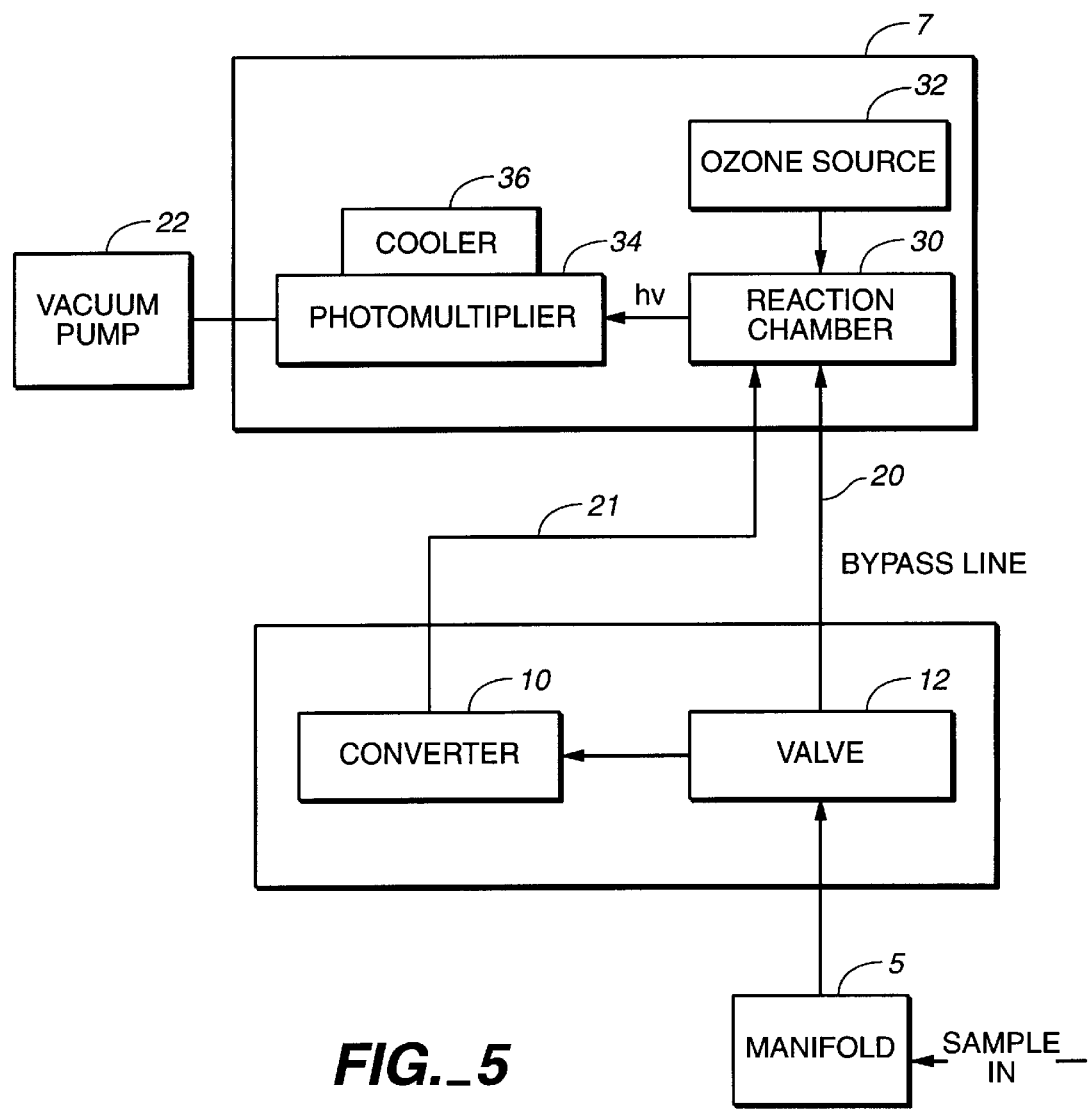
FIG._5

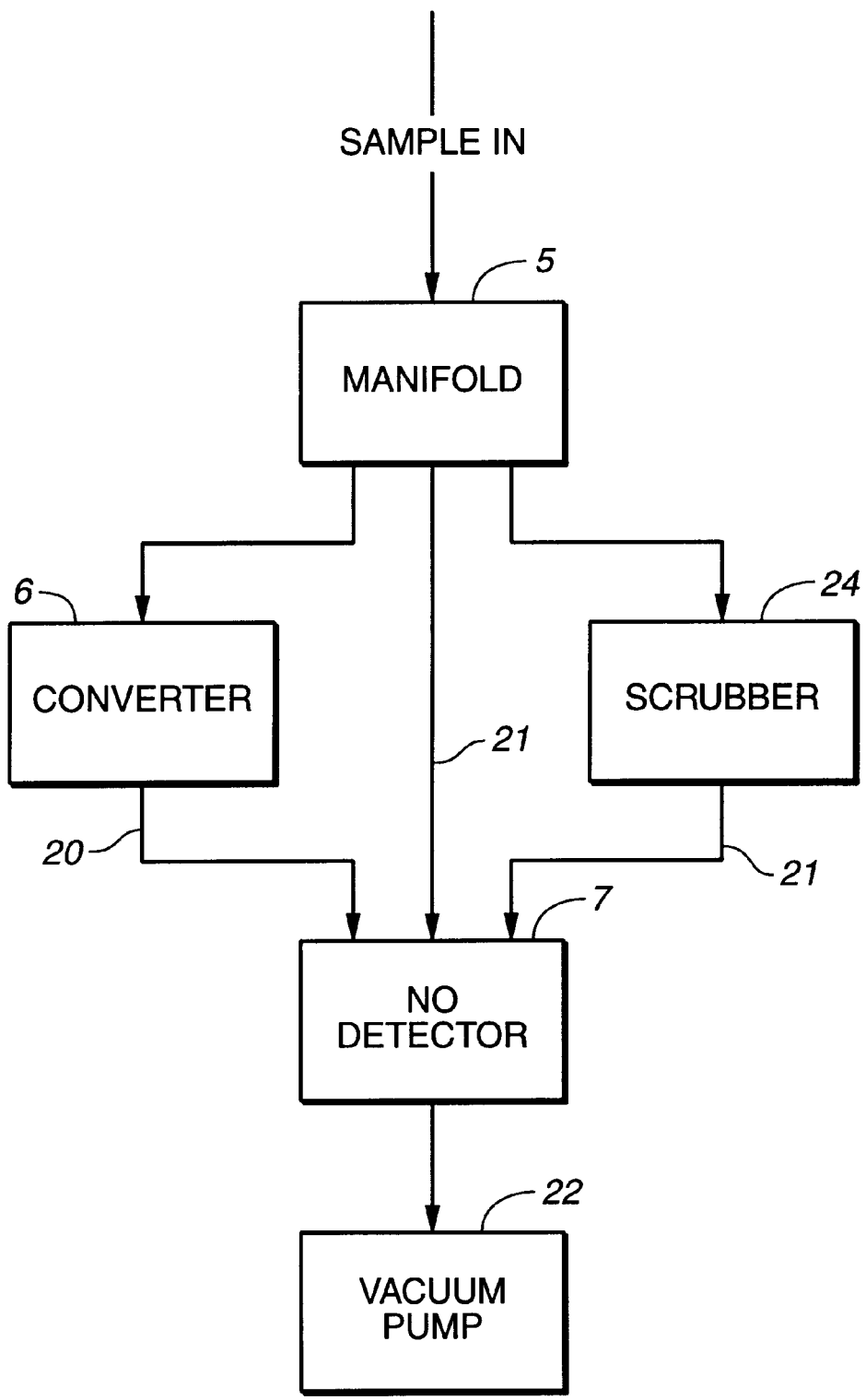
FIG._6

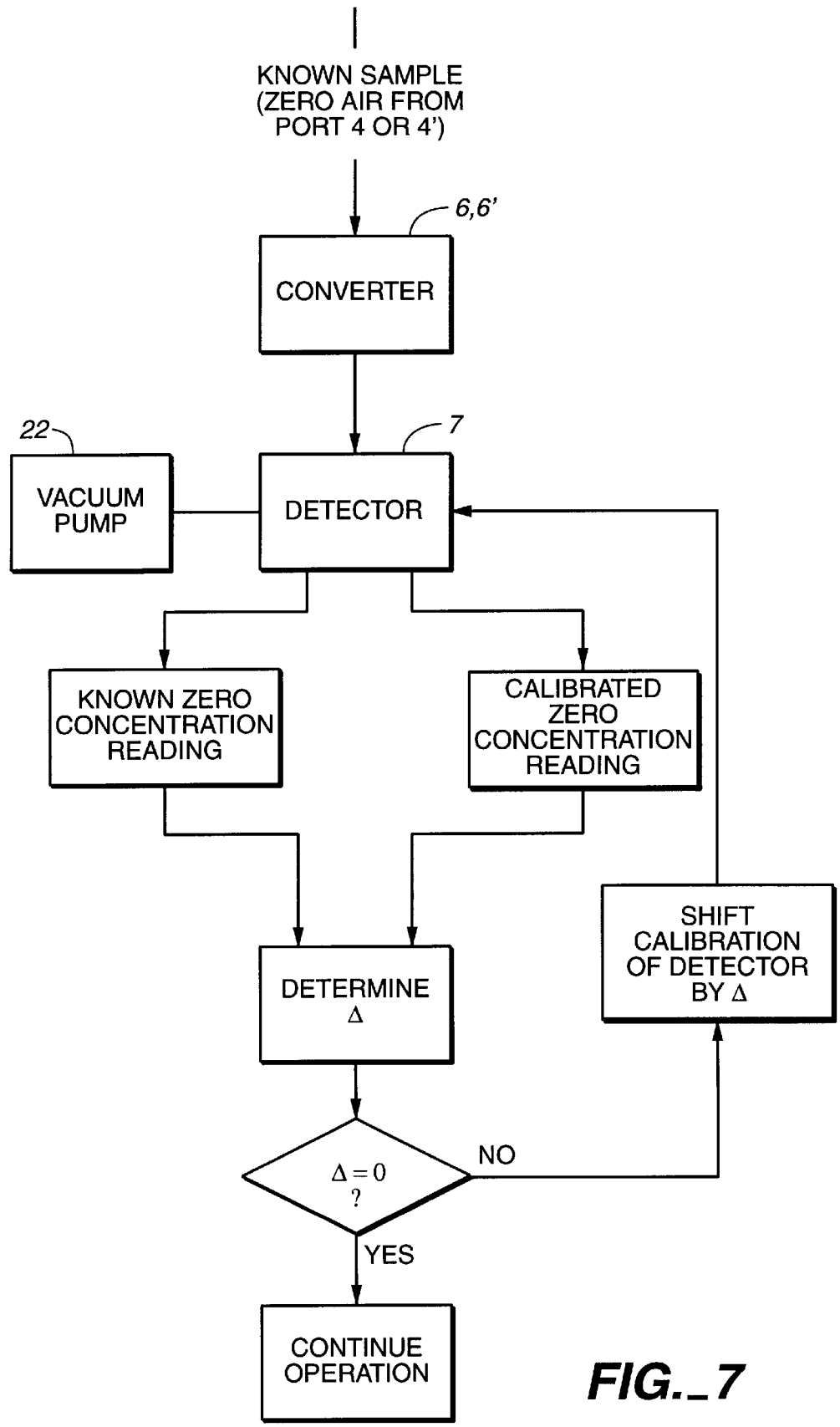
FIG._7

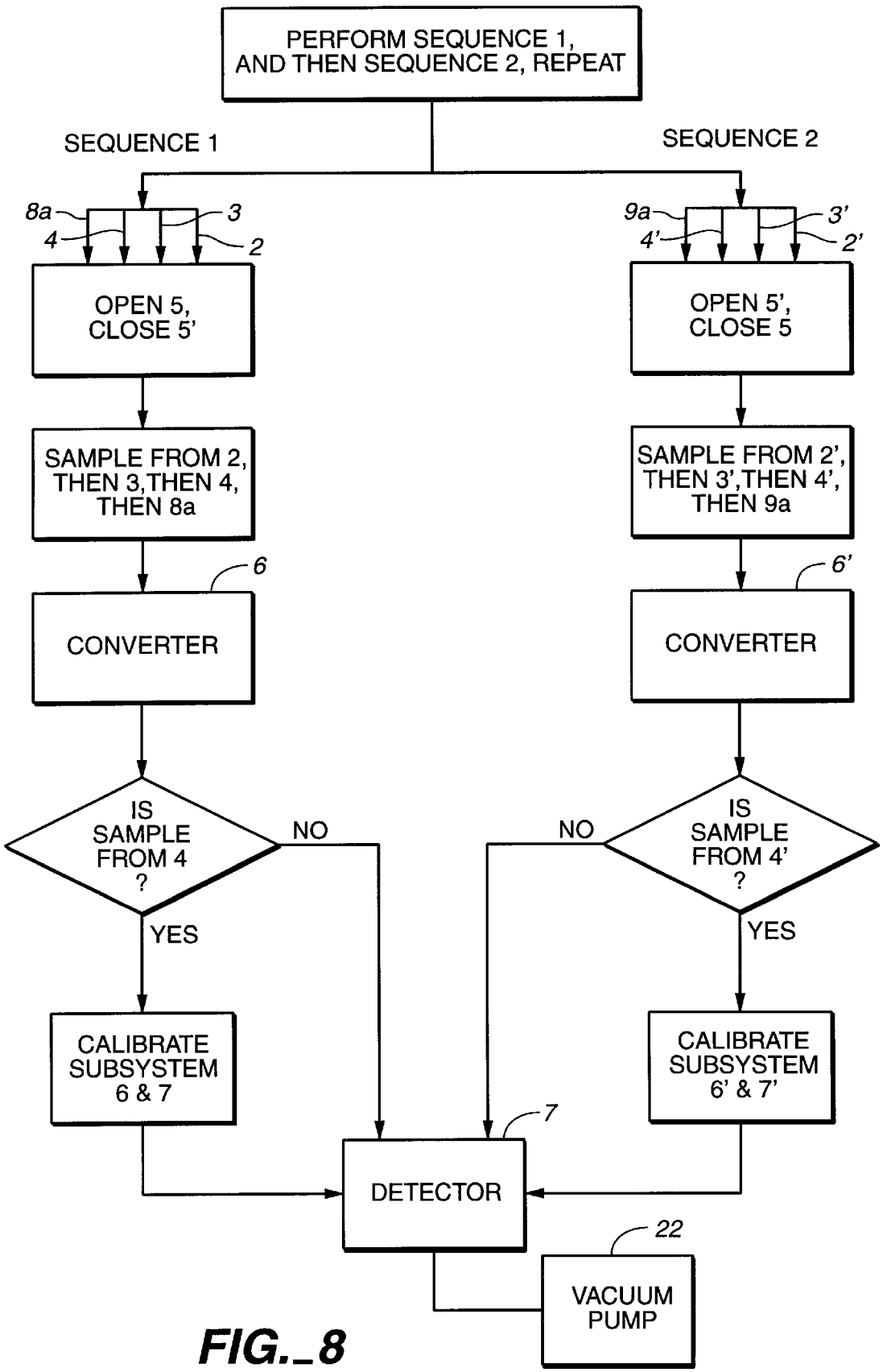
FIG._8

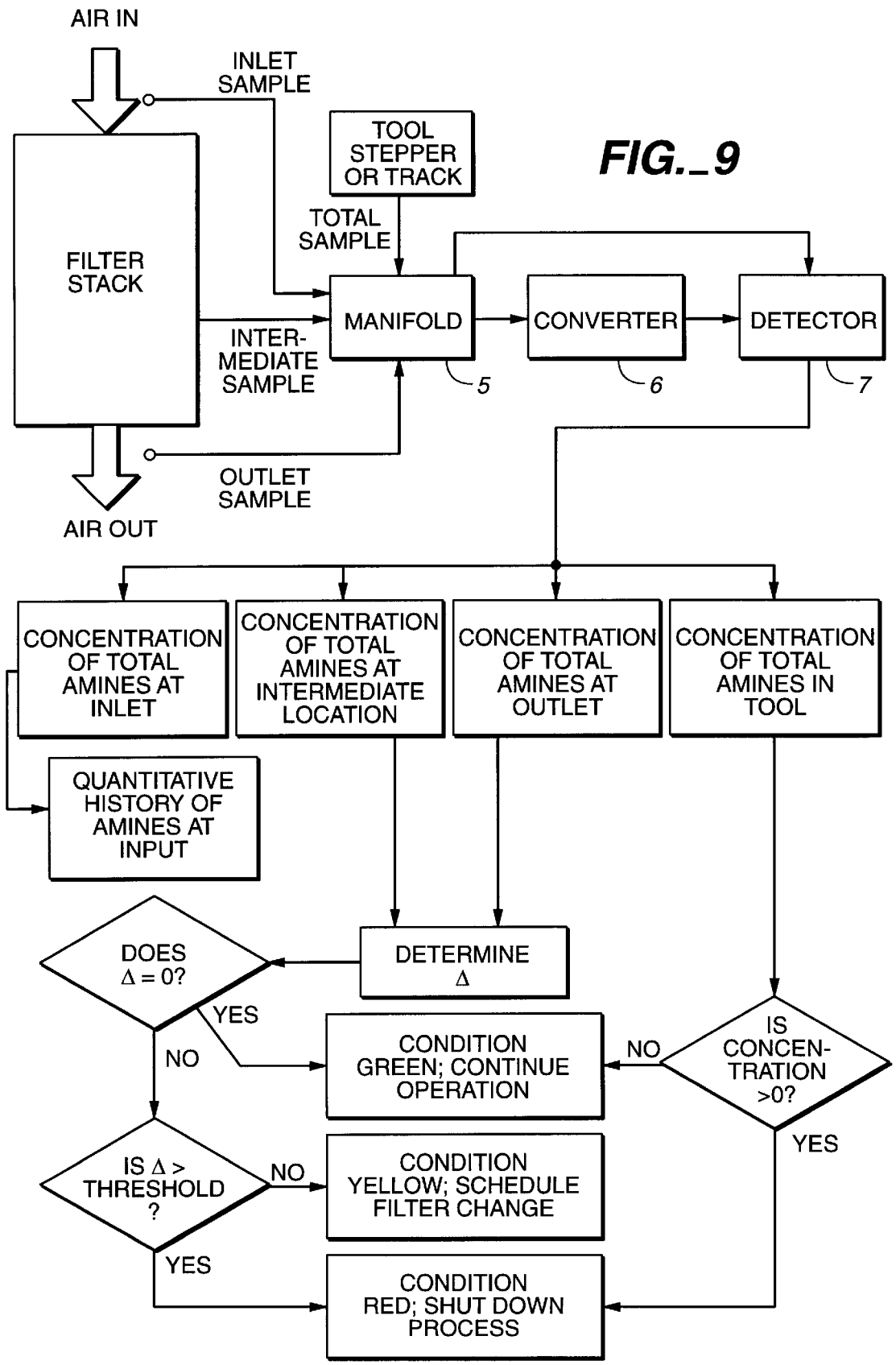
FIG._9

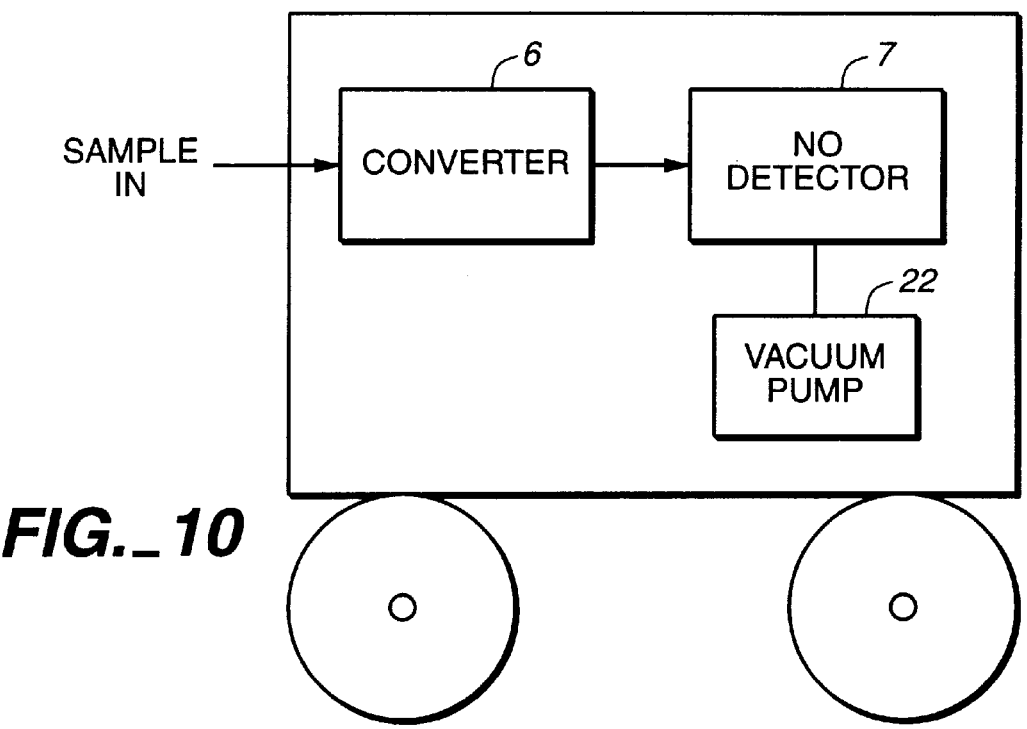
FIG._10

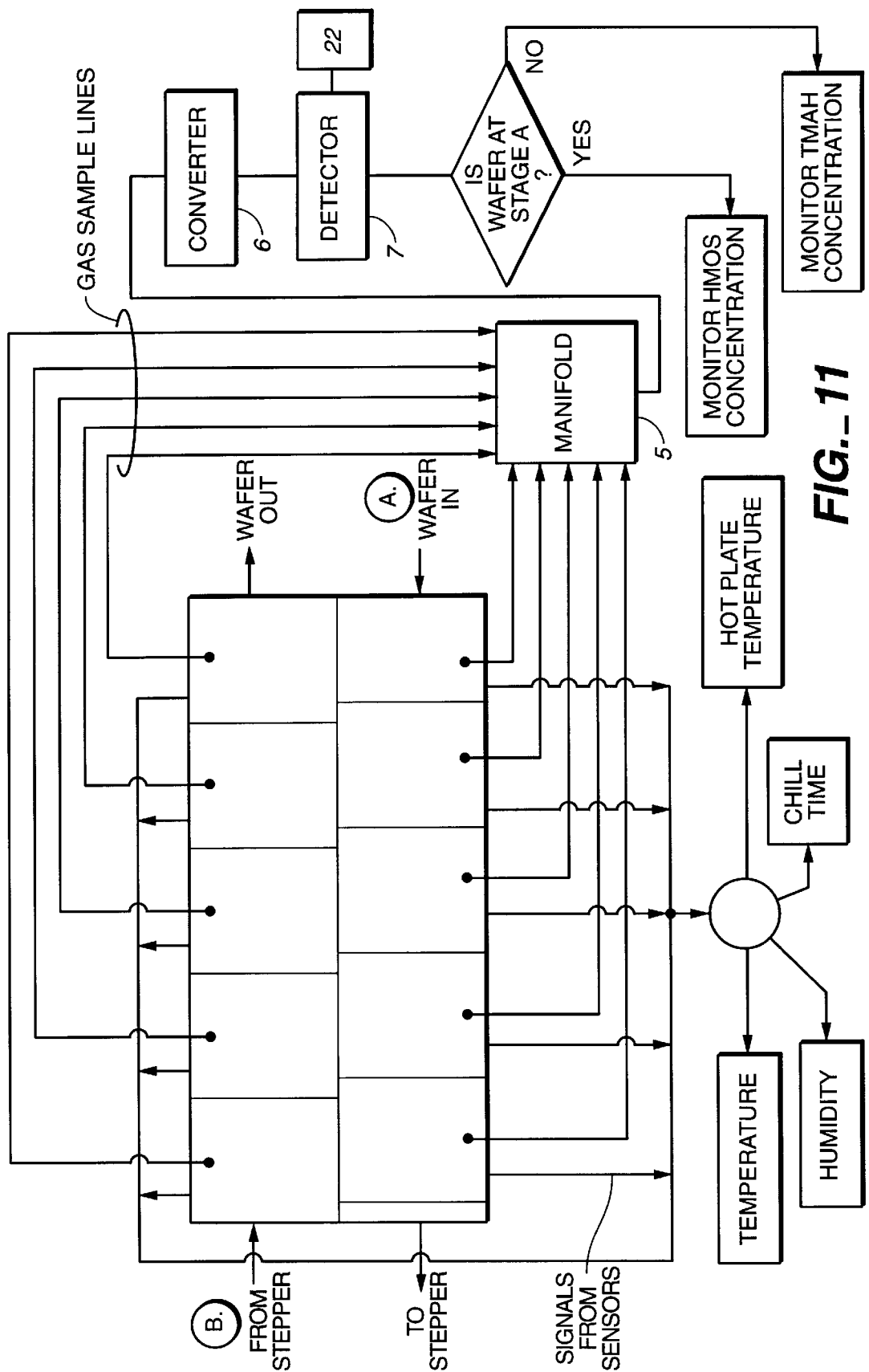
FIG._11

SYSTEM FOR DETECTING BASE CONTAMINANTS IN AIR

BACKGROUND OF THE INVENTION

The invention relates to the detection of base contaminants in air, especially amine contaminants, and to systems employing such detection, including semiconductor fabrication systems and systems for filtering air for semiconductor fabrication and other processes that require uncontaminated air of high quality.

In semiconductor manufacturing it has been found desirable to detect an organic amine such as NMP (normal methyl pyrrolidinone) or ammonia. Such a contaminant may interfere for instance with a photolithography process used in semiconductor fabrication. The base contaminant may react with protons produced as a result of exposure of a photoresist layer to light. This can interfere with proper exposure and can harm the yield of the process and the rate of production of the semiconductor wafers.

For this reason, semiconductor manufacturers have sought to measure and control the concentration of airborne molecular contamination during the critical steps of the photolithography process which are sensitive to it. A detecting instrument specific to the detection of NMP and a detecting instrument specific to the detection of ammonia have been employed in semiconductor manufacturing facilities to monitor the air quality in the vicinity of production tools.

To avoid harm to the process from NMP or ammonia, semiconductor manufacturers have used chemical filters to remove the contaminants. These filtering systems employ filter stages within an enclosure, the filter media of each stage being penetrable by air with acceptable pressure drop. As air flows through the filtering system, unwanted contaminants are retained on the chemically active surface of the various stages of the filter system.

A problem associated with such filtering systems has been to accurately predict the remaining life of the filter so that the filter media can be changed at appropriate times with minimal disruption to the use of the expensive production facility. In the case of semiconductor fabrication facilities, typically, filter life has been estimated by measuring the concentration of ammonia in the air flow associated with the filter system.

SUMMARY OF THE INVENTION

The invention is based on the realization that in semiconductor manufacturing and in certain other processes that are recognized to be sensitive to NMP, ammonia, or other amines, in reality the process is sensitive to the total proton-bonding capability of all base contaminants present, no matter what the specific identity of the contaminants. According to the invention, rather than determine the presence and concentration of each individual contaminant by a separate detector, it is realized that important advantages can be obtained by providing a detector that provides a single reading that is stoichiometrically related to the aggregate proton-bonding characteristic of various base contaminants that may be present in the monitored air. In this way a "total amine detector" is provided.

In important implementations of this idea, a system and method are provided that employ a converter to convert ammonia and other low or medium molecular weight amines present, to a single detectable gas, which is then detected. Preferably the contaminants are converted to NO (nitric oxide) molecules and the NO is detected with an $NO_x$ detector by subtracting from the total $NO_x$ reading, the $NO_x$ originally present in the sample as it was introduced into the converter. In a preferred implementation the conversion is produced by thermal oxygenation. In various specific implementations, a heated stainless steel surface, a heated quartz surface or a catalytic conversion surface is employed to accomplish the oxygenation.

According to other aspects of the invention, advantages are obtained by placing the converter near the sampling site. In various implementations, the sampling site is a stage of a process affected by the contaminant, such as the stepper or track stage of a photolithographic tool cluster, or a part of the air filtration system, or the incoming air, or a region where contamination could arise such as a chemical storage locker. In these cases, sampling lines for unconverted and converted samples extend from the local converter to a remote NO detector. In certain cases, it is also advantageous that a number of such converters are employed to provide sampling capabilities in different locations, with each converter connected to the centralized detector.

One of the advantages of having the converter near the tool or other sampling site concerns the ability to obtain rapid stabilization of the detection cycle and, correspondingly rapid accurate readings, to give early warning of any contamination problem. It is realized that amine contaminants have a high adsorption coefficient relative to the interior surfaces of typical sampling lines. Deposits of amines in long sample lines can require long periods of flushing until a stable reading is obtained. On the other hand it is realized that the converted gas, NO, has a low adsorption coefficient relative to the sample line surfaces. By localizing the NO converter at the site to be monitored, only a short sample line is subject to adsorption of amines, while the extended line between the converter and the remote detector conducts air containing non-adsorptive NO. In this manner, the sampling cycle can be of very short duration, to provide early warning for the detection of unwanted contaminants.

In semiconductor clean rooms, for instance those in which deep UV photolithography is conducted, a series of chemical filter stages is employed for the air supply. The flow of air passes successively through the filter stages to provide deep cleaning of the air to remove airborne amines.

According to another aspect of the invention, one or more conditions relevant to the operation of a total amine detection system is determined from the filter system, and in another aspect of the invention one or more conditions relevant to the operation of the filter system is monitored by the total amine detector system.

In a preferred implementation, a sampling port is located downstream of the filter system to monitor the filter output, and at least one additional sampling port is disposed between stages of the filter (at an intermediate location). In preferred arrangements another sampling port is localized upstream of the filter system to monitor the chemical contamination to which the system is being exposed over time.

To enable calibration of the zero point of a total amine detection instrument, the downstream outlet port provides zero air (air free of amine contamination) for onsite calibration of the instrument. In certain instances, the calibration is performed manually by the operator, while in other implementations the calibration proceeds automatically on a periodic or continuous basis. The fidelity of the zero air from the downstream port is guaranteed as long as the concentration of contaminants at the intermediate sampling port is also zero.

During normal use of the filter system, the difference in the concentration of the contaminants measured between an intermediate port and the downstream outlet port is zero, as the preceding stage(s) of the filter are effective to remove all amine contaminants. The detection system is arranged to measure this differential for use for determining the validity of the zero reference. When the differential becomes greater than zero, or alternatively, when the differential reaches a certain value that still predicts that the output has ceased to contain zero amines, the differential reading is taken to indicate the unreliability of the zero output of the filter for calibration purposes.

A differential reading between the outlet and an intermediate sampling point is also advantageously employed to indicate the time when the elements of the filter system should be replaced. A zero differential reading indicates all of the contaminants are still being removed by the filter stages upstream of the intermediate sampling port, while a positive value indicates that some contaminants have reached the intermediate point and can only be removed in the final stage of the filter.

Another way of predicting the time for filter replacement employs the total amine detector to detect total amines from a sample port upstream of the filtering system. This provides information regarding the past history of contaminant concentration in the airflow that has passed through the filtering system. The contamination of air entering the system may change because of the season of the year, industrial or agricultural activity in the region, or accidental spills within the facility. The overall contamination rate is monitored over time at the upstream sample port. And, by correlation of this history of contaminant loading with the past performance of the filter, as monitored at an intermediate stage, the amount of filter life remaining is projected, and the time is set when the filter elements should be changed.

In a system combining these features, information from the sampling port at the outlet of the filtering system is employed to assure that no contaminant enters the environment to be protected, the intermediate port is employed to provide for early warning, and the upstream sample is employed to provide information about background contamination and is used to determine filter performance.

In certain instances, multiple intermediate sampling ports are employed along the filtering system, to provide further information to assist in indicating when change of the filter elements should be scheduled. The intermediate port closest to the outlet can be employed to verify the fidelity of the outlet air as a zero reference for the detection system.

According to a further aspect of the invention, the same converter is used in conjunction with monitoring the performance of an air filtering system and monitoring the environment of a particular tool, or process with which the air filtering system is associated. In this arrangement, zero air calibration can be provided simultaneously for the reading for both the tool or process and the filter system. In important examples where a centralized detector serves multiple converters that monitor different regions, each subsystem of a converter and the detector is advantageously treated as a separate calibration entity that is separately calibrated using, for zero reference, a sampling port at the outlet of the filter system that serves the respective sampling region.

We will now summarize important aspects of the invention.

According to one aspect of the invention a detection system is provided for detecting base contamination at low concentrations in a gas, for instance to protect a sensitive process, characterized in that the detection system is adapted to examine multiple amines in the gas and to produce a reading stoichiometrically related to the aggregate proton-bonding characteristic of the multiple amines present.

Preferred implementations of this aspect have one or more of the following features.

The detection system is adapted to examine all air-borne amines.

The detection system includes a converter arranged to convert multiple amine contaminants in a gas to a common detectable compound, and a detector is adapted to detect that compound. The converter of the detection system is preferably adapted to form said compound by thermal conversion. Preferably the converter is adapted to oxygenate the multiple amines to NO.

Preferably the detector for a common compound to which the various amines are converted is a chemiluminescent detector, preferably the converter converts amines to NO and the detect or includes a reactor to react NO with ozone to produce photons for chemiluminescent detection.

In another preferred implementation the detector is a colorimetric detector.

In the preferred implementation the detector is controlled to detect $NO_x$ from the sample line and $NO_x$ from the converter, and is constructed to subtract $NO_x$ of the sample from the $NO_x$ reading for the converted sample to determine the total proton-bonding characteristic of the concentration of the multiple amines within the air sampled.

In certain preferred implementations the detection system includes an extended gas conduit disposed between a converter located in the vicinity of a sample region and a remote detector and the common gas, preferably No, to which the converter is adapted to convert the amines, has a relatively low adsorption coefficient relative to the interior surface of the conduit.

Preferred implementations of the detection system include a calibration system which includes a permanent connection to a source of zero air, preferably the source of zero air being the output of a chemical filter system. Preferably the chemical filter system is arranged to filter air to be exposed to a chemical process which the detection system is arranged to monitor, preferably at least one sample line of the detection system being connected to detect amine contamination of air in the filter system preceding the outlet.

In certain preferred implementations, the chemical filter system comprises a series of filter stages through which air passes, and the contaminant concentration at a location preceding the outlet is measured relative to the concentration of the contaminant at the outlet to determine when air at the outlet is valid as a zero reference, preferably the stage preceding the outlet is located immediately preceding the last filter stage of the filter system.

In another implementation, the source of zero air is a dedicated zero-air generator, the zero-air generator comprising a filter for filtering the ambient air, or a liquid scrubber solution that filters the ambient air by bubbling the air through the solution.

In certain preferred implementations, the detection system of the invention is connected to an amine air filter system to monitor remaining filter capacity, preferably the filter system being connected to monitor the output of the filter system, and to monitor air preceding the outlet of the filter system. In preferred embodiments of such a system a differential detector for measuring the difference in readings between the outlet of the filter system and an intermediate point in the filter system. Preferably the detection system is connected to monitor air entering the filter system, and the detection system is connected to monitor air samples from the inlet, the outlet and at least one intermediate position of the filter system.

In certain preferred implementations, the detector receives sample from an air filter system that supplies air to the environment of an industrial process and receives sample from a region associated with the process.

In other implementations that convert the amines to a common detectable compound, the detection system includes a plurality of converters, a single detector and valving for alternatively connecting respective converters to the detector. Preferably for each converter, two conduits extend to the detector, one comprising a sample conduit sampling the gas prior to entry to the respective converter, and the other a converted sample conduit conveying the common detectable compound from the converter to the detector. Preferably the detector is connected to a vacuum pump employed to provide air flows of converted and unconverted sample gases to the detector.

Preferably the detection system with this vacuum pump includes an impinger comprising a tube containing liquid scrubbing solution, the impinger being connectable at one end to the pump to draw unconverted sample air through the liquid, to provide a grab sample of contaminants in the sample air.

In another implementation the detection system includes an additional line to direct unconverted gas through a scrubber to the detector to remove amines from the gas, preferably the concentration of $NO_x$ detected in the scrubbed gas by the detector being compared with the concentration of $NO_x$ in the unconverted, unscrubbed sample gas to verify the fidelity of the $NO_x$ readings of the detector.

In other preferred implementations, the detection system includes a calibration system constructed to establish separate calibration values in respect of each subsystem comprising the detector and a respective converter, preferably including a separate source of zero air for calibrating each respective subsystem, preferably for each subsystem, the output of a chemical air filter related to air being sampled for the respective converter being employed as a zero air reference.

Preferably at least one detection subsystem receives sample from an air filter system that supplies air to the environment of an industrial process and at least one detection subsystem receives sample from a region associated with the process. Preferably different steps of the industrial process have respectively different chemical air filter systems, and different detection subsystems are connected to sample the different steps and associated air filters.

In certain preferred implementations, the detection system is combined with a photolithographic semiconductor production system. Preferably the detection system monitors air at a stepper of the production system, air at a coat and develop track of the production system, air exposed to the semiconductor work processes, the remaining filter life of an air filter system supplying air to the production system, contaminant concentrations at a stepper and a coat and develop track of the production system, and the difference between total amine concentration at the outlet of an air filter system and at an intermediate sample position of the air filter system, preferably to signal the replacement of filter elements of the filter system when the difference is above a specified threshold.

In another implementation for a method of industrial process monitoring, the detection system is employed to monitor the presence of total amine contaminants in the air that can adversely affect the process, preferably a deep UV photolithography process.

In another preferred implementation, the detection system comprises a converter adapted to convert to NO multiple amines present in an air sample, a chemiluminescence detector constructed to react the NO resulting from the amines to produce a reaction product having an excited state, and a photodetector responsive to photons emitted from the reaction product to determine the proton-bonding characteristic of the multiple amines present, preferably to monitor air quality for an environment of a deep UV photolithography process, the system having a sensitivity for 1 ppb or better of amine contaminants.

Preferably the converter is located near a stage of the process, the detector is located at a remote location, and sample lines conducting unconverted sample and converted sample extend between the converter and detector.

Preferably the photodetector is a photomultiplier tube, and a cooler is arranged to cool the tube to achieve sensitivity of at least about 1 ppb.

In other preferred implementations, the detection system monitors the total amine concentration at selected stages of a multistage manufacturing process, preferably the detection system monitors the total amine concentration of a coat and develop track tool in a deep UV photolithography process, preferably the concentration of an adhesive promoter employed during the stage of laying the photoresist at the track, and the concentration of a chemical employed during the developing stage at the track.

In another implementation a single detector is connected to monitor both the concentration of an adhesive promoter employed during the stage of laying the photoresist at the coat and develop track and the concentration of a chemical employed during the developing stage at the track.

In certain other implementations, the detection system is constructed as a mobile unit for detecting leaks in a multistage manufacturing process, preferably to localize leaks in regions of high amine contamination in a deep UV photolithography process.

In other implementations, the detection system monitors the total base loading within a clean room of a fabrication facility and provides a single reading for the total base loading for purposes of certifying the clean room.

And in another implementation, the detection system monitors filter performance of a filter in either the make-up or recirculation air supplying a cleanroom, preferably to monitor total amines both upstream and downstream of a filter system comprising either a lone filter stage or a series or parallel arrangement of filter stages in the make-up or recirculation air system of the cleanroom.

BRIEF DESCRIPTION OF THE DRAWINGS

FIG. 1 is a plan view of a deep UV photolithography processing facility employing a contaminant detection system;

FIG. 2 is a diagrammatic view of parallel trays of filter media;

FIG. 3 is a diagrammatic view of an impinger drawing unconverted sample gas;

FIG. 4 is an enlarged view of the filtration tower shown in FIG. 1;

FIG. 5 is a diagrammatic view of a converter-detector subsystem of the detection system of claim 1;

FIG. 6 is a diagrammatic view of the converter-detector subsystem of FIG. 5 adapted to include a scrubber;

FIG. 7 is a flow diagram illustrating the process of calibrating the detection system of FIG. 1;

FIG. 8 is a flow diagram illustrating the continuous operation and calibration of the embodiment of FIG. 1;

FIG. 9 is a flow diagram illustrating the monitoring and control of the processing tools and filtration system of the embodiment of FIG. 1;

FIG. 10 is a diagrammatic view of a total amine detector as a mobile detection unit; and FIG. 11 is a diagrammatic view of a photolithographic system in which a total amine detector is combined with a track.

DESCRIPTION OF THE PREFERRED EMBODIMENTS

In FIG. 1 a photolithography tool cluster is shown for the production of semiconductor wafers. The cluster consists of two tools, stepper, 8, and track, 9. Each of these tools is supplied by a separate clean air filtration system, 1a and 1', respectively. The filtration tower comprises a metal enclosure 10 and a set of spaced apart chemically active filter stages 12, 14, 16, 18 installed in series within the enclosure. As depicted in FIG. 1, the air enters at 20, at the top of the tower, the air being supplied from either outside the fabrication facility or from within the facility, or from within the clean room or the tool itself.

The filters are composed of chemically active composite materials, typically nonwoven fabric media to which are bound activated carbon particles that have been treated to remove ammonia and organic amines. The filter media is typically arranged as a set of pleats in the enclosure. An example of such filter media is known by the trademark Vaporsorb™, produced by the Assignee, Extraction Systems Inc. of Franklin, Mass.

In another embodiment of the invention, the converter-detector is employed to monitor filter performance of a filter deployed in either the make-up or recirculation air supplying a cleanroom. In this case, the converter-detector is employed in such a manner as to monitor total amines both upstream and downstream of a filter deployed either alone, or in-series in the make-up or recirculation air system of the cleanroom.

In implementations of certain aspects of the invention, other filter media are employed. Certain examples include: parallel trays of loose activated carbon particles produced by e.g. Donaldson Company; extruded carbon blocks using a dry thermoplastic adhesive as the binding agent as produced by e.g. Flanders Filters, KX Industries, Peneer Industries; thin extruded carbon blocks manifest as a fabric as manufactured by e.g. KX Industries; media made by the modification of the chemical properties of the fiber structure as produced by e.g. Ebara Ltd. and Takuma Ltd.; and carbon fiber structures as produced by e.g. Kondo Limited; and carbon particle sheet media produced by e.g. Hoechst-Celanese.

For each filtration tower, 1 and 1', there is, respectively, an upstream sampling port, 2, 2', a downstream sampling port, 4, 4', and an intermediate sampling port, 3, 3'. Sampling ports 8a and 9a are likewise provided for the stepper 8 and track 9, respectively. For each filter and tool combination, there is one converter, 6 (for the stepper 8) and 6' (for the track 9). These two converters, 6 and 6a, are connected to a common, remotely located $NO_x$ detector, 7. The detector, for instance, may be Model 17 available from Thermo Environmental Instruments Inc. and the converter may be obtained from Thermo Environmental Instruments Inc. or from other converter manufacturers.

A remotely controlled manifold, 5, 5', is associated with each converter and via respective sample lines directs to the converter a sample from the tool, the inlet stream to the filter, the outlet stream of the filter, and the intermediate filter port, according to a sequence controlled by a computer 51. Likewise, through associated direct sample lines, unconverted samples from each port are directed to the detector 7. Within the converter, all the amines in each gas sample are converted to NO by thermal oxygenation, for example,

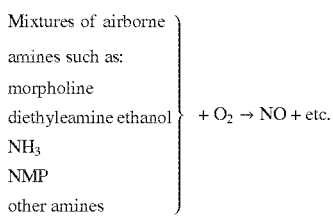

The converted gas and the unconverted sample air are directed to the detector by air flows maintained by a vacuum pump 22 located downstream of the detector 7.

The inflow to the filtration system typically has a certain amount of $NO_x$ in it. For each sampling port, the bypass line that bypasses the converter enables the detector 7 to detect the $NO_x$ inlet value at each respective sample port in a correlated manner to the detection of the $NO_x$ value in the converted gas coming from the same ports. The difference in the $NO_x$ concentration between the two lines for a respective port yields a reading of the total amines present, by the equivalent NO value. This value is stoichiometrically related to the aggregate proton-bonding characteristic of all the amines present in the sample.

In addition to the detection of total amines, by suitable adaptations, NO and $NO_2$ concentrations in the unfiltered air are readily determined by the detector as well. For certain applications, it is desirable to know the NO and $NO_2$ present.

In another embodiment, an impinger 23 is employed to identify possible contaminants in the unconverted sample air, as shown in FIG. 3. The impinger consists of a glass or quartz tube holding a liquid. In this embodiment, vacuum pump 22 and an associated calibrated flow controller are employed to draw sample air through the liquid to take a grab sample. The grab sample is then analyzed or subjected to real-time calorimetric analysis, providing a quantitative assessment of the amine contaminants in the sample air.

Referring to FIG. 4, a filtration tower 1 is shown with a corresponding computer controlled manifold 5 and converter 6. The sampling manifold, 5, directs the specified sample to the converter while it directs a respective unconverted sample directly to the detector. Two sampling lines 20, 21 thus extend to the detector, for distances as long as, for example, 1000 feet. The length of the sampling lines is not critical because, as previously mentioned, the converted gas, NO, has a low adsorption coefficient relative to the interior surface of sampling lines, constructed, for example, of PTFE (Teflon™ of dupont) and stainless steel, whereas, in the case of the sample inlet gas, no measurement of amines is made so deposits in the sample lines are of no consequence.

In an alternate embodiment, the converter is not located near the sampling region, and silica-steel sampling lines are employed. These lines are made of stainless steel, and the inner surfaces are coated with a thin layer of fused silica. The inner surfaces are nonporous, chemically inert and have a low adsorption coefficient with respect to amines.

In the preferred embodiment, there is a heated stainless steel surface (at a temperature of 500° C. to 1000° C.) within the converter to which the sample gas is passed. This enables oxygenation with oxygen contained in the air sample. Depending upon the particular set of amines that may be expected in the installation, the precise temperature of the converter surface is determined to optimize the most efficient conversion of the amines. In other embodiments, a heated quartz surface is employed. In another embodiment a catalytic surface is provided for oxygenation to occur through catalysis, in which the surface temperature can be lower. The appropriate conversion technique is determined by the desired application, taking into account cost and conditions of use.

The $NO_x$ detector 7, or analytical module, is illustrated in FIG. 5, in conjunction with converter 6. Shown are the two sampling lines 20, 21 extending, in this case, from the converter to the detector. By action of selection valve 12, within the converter, line 20 bypasses the converter reaction unit 10 while line 21 provides converted gas to the detector. In the presently preferred implementations, the detector employs chemiluminescence for $NO_x$ detection. For this purpose NO is caused to react in the reaction chamber 30 with ozone, namely,

$$NO+O_3 \rightarrow NO_2^* + O_2,$$

where the ozone is provided by an internal ozone generator 32. This produces electronically excited $NO_2$ molecules which in returning to the ground state emit photons, hv, that are detected by appropriately cooled photomultiplier 34. The reaction is given by the expression

$$NO_2 \rightarrow NO_2^* + h\nu.$$

Associated electronics amplifies the signal from the photomultiplier (PMT) to provide a reading of $NO_x$ concentration.

The ozone reaction is conducted under conditions that prevent conversion of amines to NO, so that the $NO_x$ reading of the sample arriving unconverted from the sample port $NO_x(u)$ is not disturbed either by amines in the air sample or amines adhered to the inner surfaces of the sample conduit. Total amine detection, $A_T$, is then determined by comparison of the reading for the unconverted sample $NO_x(u)$ with the reading $NO_x(c)$ for the converted sample according to the expression $$NO_x(u) - NO_x(c) = \Delta NO_x = A_T.$$

To achieve the needed sensitivity for current deep UV photolithographic processes with presently available photomultipliers, the photomultiplier tube is cooled at least to −5° C. To achieve sensitivities required for next generation fine resolution deep UV photolithography in semiconductor manufacturing, the tube is cooled to −15° C. by associated thermoelectric cooler 36. Moreover, since there is significant variation in the sensitivity of photomultiplier tubes produced by the same manufacturer, the analyzer sensitivity is further increased by testing and choosing an optimum photmultiplier tube for the performance required. In other implementations, $NO_x$ is detected by calorimetric methods, available e.g. from Tytronics, Inc. of Bedford, Mass., or other methods using continuous inline sampling.

In other embodiments of the invention, additional sample lines are employed, as illustrated in FIG. 6. For instance, in an embodiment, in addition to sampling lines 20 and 21, another line is employed to direct to the detector sample gas from which amines have been removed. An unconverted sample is directed from the sampling manifold 5 to a scrubber 24. The scrubber employs chemically treated carbon filters to scrub out amines from the sample, or the amines are scrubbed out by bubbling the sample air through a liquid scrubber solution. The $NO_x$ concentration in the scrubbed sample is compared with that of the unconverted sample from sampling line 20. If the two readings are the same or within a predetermined differential threshold, the method provides further verification that the $NO_x$ readings are correct.

According to another aspect of the invention, in an instrument associated with more than one converter, each converter-detector subsystem is considered as a single instrument, which is calibrated independently of the other converter-detector subsystems. In the preferred embodiment illustrated in FIG. 1, there are two converter-detector subsystems: one subsystem serves the track and air filter system 1 and the other subsystem serves the stepper and it's air filter system 1a. For calibration purposes, zero air is provided by filter system 1 for the stepper subsystem and by filter system 1a for the track subsystem. By having the converter near the sampling area, the length of the sampling lines exposed to amines is reduced, which increases the response time of the system.

To calibrate each converter-detector subsystem, two or more samples of known concentration of contaminants are provided to the instrument, as illustrated in FIG. 7. The instrument response is then compared with the known concentrations, and a calibration curve is generated and either manually or electronically, through the software, associated with the instrument to provide corrections to the instrument's response. In general, the instrument's response over the concentration range remains stable for an extended period. The instrument is sensitive, however, to zero calibration, for reasons such as drift of the PMT and the curve must be shifted relative to the true zero reading as it varies over time. Because harmful contaminant concentrations are extremely low (on the order of 1 ppb or better) in photolithography processing, in preferred systems, the zero calibration is performed regularly (at least once a day) to assure the fidelity of the zero reading. In a preferred implementation, the detection system is arranged to operate continuously, as shown in FIG. 8, to performing a total amine detection for each of the sampling ports in turn, and conducting two calibrations each cycle, one with respect to each of the converters with which the detector operates.

In the preferred embodiment, the zero air employed for calibration is provided by the outlet ports 4 (and 4') of the filtration system (see FIG. 1). The instrument is then instructed to provide a zero reading for the calibration sample. In the case that the difference between the total amine reading for the outlet port 4 and the sample at the intermediate port 3 is not greater than zero, the sample from the outlet port 4 is employed to establish zero air. In another preferred embodiment, a sampling port located just preceding the last filter stage is employed to verify that the zero air from the output of the filter stack is in fact zero air. Also, in an alternate embodiment, a built-in dedicated zero air generator is employed. The generator provides zero air by either filtering the ambient air or by bubbling air through a liquid scrubber solution.

An external computer, preferably situated outside the clean room in which the tools are located, is employed to control the operation and monitor the entire photolithography process. The software is customized for the required application. Performance data is provided to the computer to provide an archival data base to be employed to give the contamination history of the tool clusters.

Based on the particular ports being sampled, the software employed in the operation of the instrument determines which converter-detector subsystem is to be calibrated and the appropriate source of zero air for calibration purposes. The software also designates which calibration curve to employ. As the detection system is calibrated and new zero readings are determined, the calibration curves are adjusted accordingly.

In a desired application, control instrumentation, as illustrated in FIG. 9, monitors the performance of the filtering system and the level of contamination at the track and stepper tools. Should a reading from either the stepper or track exceed a predetermined threshold, an alarm is enabled and the process is immediately shut down. However, by use of this detection system, the occurrence of such an emergency can normally be avoided.

As shown in FIG. 9, the filtering system is continuously monitored in real time as follows: the sample at the inlet to the filter system, over time, provides a quantitative history of the input of amines or other Bronstead base contaminants to the filter. By use of samples drawn from the intermediate position along the filter system as well as from the outlet of the filter stack, and measuring the difference in concentration levels from these locations, one of the following steps is caused to occur: if the difference is zero (condition green) and the total amine or Bronstead base concentration at the tool is within operating limits, then the operation continues with no interruption; when the difference is greater than zero, the difference is compared with a predetermined threshold; if the threshold is not exceeded (condition yellow), operation continues but a filter replacement is scheduled; if the threshold is exceeded, or if the total amine detected at the tool exceeds operating limits (condition red) the operation is immediately shut down.

In another embodiment, there are three or more converters remotely located at various locations in the fabrication facility. A converter is employed to monitor the general conditions in the clean room, pair a of converters is employed to monitor the contamination around a different tool cluster, and another converter is employed to monitor the contamination level within a chemical storage cabinet, to provide early indication of chemical spills.

In another implementation shown in FIG. 10, the converter-detector instrument is constructed as a mobile leak detector. The mobile unit is moved to selected regions of the fabrication facility to seek possible areas of contamination leaks. By following an escalating amine concentration trend, the mobile unit localizes the source of the contamination.

As illustrated in FIG. 11, the invention , in another preferred embodiment, is combined with a multi-point sampling system of an array of sensors to monitor the operating status of a track, including temperature, temperature of the hot plate, time on the chill plate, exposure time, etc. A total amine detector monitors process contaminants in air such as the concentration of an adhesion promoter, such as hexamethyldisilozane (HMDS), during the coa ting stage where photoresist is applied to the semiconductor wafers. The wafers are then sent to the stepper for exposure and subsequently brought back to the track for developing. During this stage, another, or the same, total amine detector monitors the concentration of another possibly internally processed chemical contaminant, such as tetramethylammoniumhydroxide (TMAH), employed in the developing stage.

The present invention enables, in its total amine reading, the simultaneous detection of NMP and ammonia, typically monitored previously with separate detectors. The invention enables detection, in its total amine reading of other amines that are known to be harmful to the photolithography process, such as morpholine, diethylamine ethanol, and cyclohexylamine, agents which are commonly used to inhibit corrosion in high humidity regions. Amines from the facility cafeteria, especially seafood, are also included in the detection as well as amines from the breath of the facility workers, that can create high levels of amine contamination, depending upon diet and smoking habits. As has been explained, the system as illustrated converts substantially all such air-borne amines to a common detectable compound and detects it to indicate the level of hydrogen-bonding contaminants. If high concentrations of the contaminants are detected, by grab sampling techniques, the exact sources of the contamination can be determined and remedied.

Another advantageous aspect of the invention is its adaptation to the certification process of clean rooms. Heretofore, during the certification process, each individual molecular base present in the clean room had to be detected by separate detectors. The concentrations were summed providing a number indicating the total base loading in the clean room. For instance, if three bases were present, each with a concentration of 10,000 ppt, the clean room rating would be MB30,000 (or 30,000 ppt). The present invention solves the problem of detecting individual bases by providing the total base loading within a clean room with a single reading.

Certain broad aspects of the invention can be realized in other ways. For instance the total amine detector may be based on wet chemistry instead of thermal conversion. The common compound to which multiple base contaminants may be thermally converted may be a compound other than NO. Detection techniques different from chemiluminescence can be employed, etc.

What is claimed is:

1. A detection system for detecting base contamination at low concentrations in gas, comprising:

an amines remover having and upstream side and a downstream side;

a converter system being configured to convert amines contained in received air samples into $NO_x$;

a first sample line configured to deliver an air sample from the upstream side of the amines remover to the converter and a second sample line configured to deliver an air sample from the downstream side of the amines remover to the converter;

a detector system located downstream of the converter system and coupled to receive converted gas samples from the converter system, the detector system being configured to produce signals representative of the NOx concentration contained in converted gas samples passing therethrough.

2. The detection system of claim 1 wherein the first and second sample line share a common converter system and a common detector system.

3. The detection system of claim 1 wherein the detector system is coupled to the converter system.

4. The detection system of claim 1 further comprising a vacuum pump coupled to the detector system.

5. The detection system of claim 1 wherein the converter system is arranged to convert multiple amines in a gas into a common detectable compound, and the detector system is adapted to detect the common detectable compound produced by the converter system.

6. The detection system of claim 1 wherein the detector system is adapted to oxygenate multiple amines into NO.

7. The detection system of claim 1 wherein the detector system is a chemiluminescent NO detector.

8. The detection system of claim 1 wherein the amines remover comprises a chemical filter.

9. The detection system of claim 1 wherein the amines remover comprises a liquid scrubber solution.

10. The detection system of claim 1 further comprising a valve for alternately connecting the first and second samples lines to the converter system.

11. The detection system of claim 1 wherein the converter system includes a plurality of converter systems and the detector system includes a single detector, and further comprising valving for alternatively connecting the converter systems to the detector.

12. The detection system of claim 11 wherein the detector includes a calibration system constructed to establish calibration values for the detector.

13. The detection system of claim 12 including a separate source of zero air for calibrating each respective subsystem.

14. The detection system of claim 1 combined with a photolithographic semiconductor production system.

15. The combination of claim 14 connected to monitor air at a stepper of the production system.

16. The combination of claim 14 connected to monitor air at a coat and develop photolithography track of the production system.

17. The combination of claim 14 connected to monitor remaining filter life of an air filter-system supplying air to said production system and contaminant concentrations at a stepper and coat and develop track of said production system.

18. The detection system of claim 1 adapted to monitor air quality for an environment of a deep UV photolithography process, the system having a sensitivity for 1 ppb or better of amine contaminants.

19. The detection system of claim 18 in which the photodetector is a photomultiplier tube, and a cooler is arranged to cool the tube to achieve sensitivity of at least about 1 ppb.

20. The detection system of claim 1 connected to monitor the total amine concentration at selected stages of a multi-stage manufacturing process.

21. The detection system of claim 20 connected to monitor the total amine concentration of a coat and develop track tool in a deep UV photolithography process.

22. The detection system of claim 1 wherein each of the first and second sample lines has an interior surface with a low adsorption coefficient for amines.

23. The detection system of claim 1 wherein each of the first and second sample lines has an interior surface comprising silica.

24. The detection system of claim 1 wherein the detector system determines the concentration of amines based upon a detector system signal produced from a gas sample received from the first sample line and a detector system signal produced for a gas sample received from the second sample line.

* * * * *